Jan. 20, 1959 P. ECKE Plant Pat. 1,802
POINSETTIA PLANT
Filed April 28, 1958
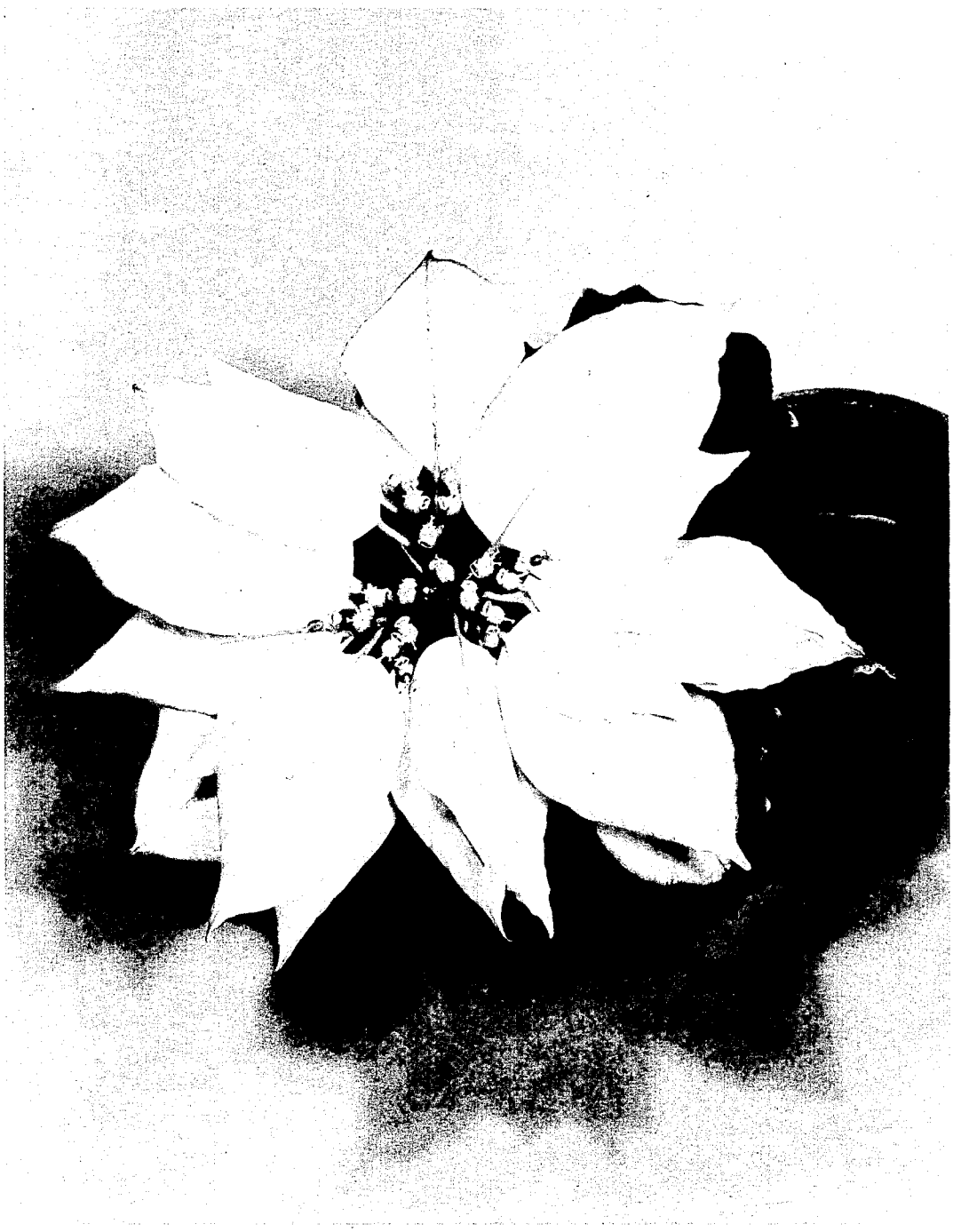
INVENTOR
Paul Ecke
by [illegible] Graham
Attorney United States Patent Office Plant Pat. 1,802
Patented Jan. 20, 1959

1,802

POINSETTIA PLANT

Paul Ecke, Encinitas, Calif.

Application April 28, 1958, Serial No. 731,556

1 Claim. (Cl. 47—60)

The subject of the present invention or discovery is a new and distinct variety of poinsettia plant (*Euphorbia pulcherrima*) originating as a cultivated sport.

Broadly, this new variety of poinsettia plant is distinguishable from its parent plant, as well as from other known varieties, mainly in the shape, color and arrangement of the bracts which are predominantly a pale greenish tint of creamy white color, and of substantially greater transverse width than known varieties, the greater-width bracts being sufficiently profuse in number to relatively overlap in layers, and sufficiently spaced radially around an inflorescence by relatively short petioles to form a wreath-like involucre.

The accompanying illustration, forming a part of this application, graphically shows this new variety in color and more particularly the bract involucre, inflorescence and foliage leaves at full maturity, and the characteristics which differentiate this new variety.

The colors referred to in the color tabulation herein correspond substantially with those shown in "Dictionary of Color" by Maerz and Paul (first edition, 1930), and are more particularly identified by the color plate of said color standard by recapitulation in tabular form herein.

The following is a detailed description of this new variety of poinsettia plant.

*Parentage*

This new variety was originated, cultivated and discovered by me in a cultivated area of a glass house or greenhouse at my experimental and growing gardens at Encinitas, San Diego County, California. It originated as a cultivated sport of poinsettia plant of the variety commonly known as "Ecke White" poinsettia plant, which is not patented but has been known in the trade by that name for many years, and is also referred to by that nomenclature in pertinent literature such as United States Plant Patent No. 1,085, dated April 22, 1952, and bulletins of the agricultural experiment stations of several States, such as in "Greenhouse Potted Plants," Ohio Agricultural Experiment Station, Wooster, Ohio (September 1955).

*Propagation*

This new variety of poinsettia plant has been asexually reproduced and cultivated by me in my said greenhouse or glass house by cuttings, and successive reproductions thereof have remained true to type and the herein described characteristics through the propagation, cultivation and asexual reproduction of several generations of this new variety, and it has shown its qualities and characteristics to be permanently fixed. In asexually reproducing this new variety I have found it satisfactory and efficient to cut pieces of stalk of soft wood substantially six inches in length in the months of June, July and August, embedding one end of such cuttings in beds of sand in my glass house. After three or four weeks the cuttings are well rooted and may be transferred to individual pots. My experience has been that the optimum temperature for growing under glass is of the order of sixty to sixty-five degrees F., night temperature, the daytime temperature being warmer and subject to the varying conditions of light, heating, thickness of glass, cultivation, character of soil, fertilizer and pruning or pinching.

*Habits of growth*

This new variety of plant will mature to optimum from about December first to mid-December, retaining bracts and leaf foliage for substantially two months, after which the plant will normally go dormant for about three months until the following spring.

*Structure*

The peduncles which branch from the main trunk are usually relatively short, stiff and very strong, and the internode space between foliage leaves is relatively short compared with other varieties, the normal result being that the height of the plant is lessened, being from four to five feet of luxuriant wide bushy growth, its height and luxuriant growth depending appreciably on the type of pruning or pinching, cultivation and fertilization, all of which have a tendency to cause a growth of side shoots which provide a luxuriant wide body growth relatively shorter in height than the normal poinsettia plant. At the top or axil end of the peduncles a node is formed from which grow pale green bract-bearing branches or stem-like spurs which bear the inflorescence and the bract involucre.

*Foliage leaves*

The foliage leaves are arranged around the peduncle, the nodes being more closely spaced than usual. As is characteristic of many varieties of poinsettia plants, the foliage leaves are not entirely uniform in shape, but may be described as generally ovate, and having points at the edges toward the outer end. They have herringbone venation. The color of the foliage leaves may be broadly described as dark ivy green.

*Bracts*

The bracts which are the predominating novelty of the present new variety are slightly thicker than usual and tend toward the sub-coriaceous. They are formed in an involucre or wreath radiating from the bract-bearing spurs or branches on quite short petioles. The involucre forms a profusion of bracts, the majority of which are relatively large, which causes them to overlie in several layers and overlap at adjacent edges, providing an annular wreath with a relatively small opening at its center due to the short petioles.

The large bracts, in planar contour, are elongated and prolately ovate-accuminate; they are numerically greater in number of individual bracts than any of the known varieties of white poinsettias which have broad prolately ovate-acuminate bracts, the involucre having a predominating majority of the individual larger bracts of greater axial length and greater transverse width, greater thickness and greater individual planar area than known varieties of white poinsettias, thus providing a wide diameter to the involucre ranging up to six to eight inches.

At the optimum of their maturity the bracts may be generally and broadly described as predominantly a pale greenish tint of creamy white with some, but not all, of the bracts having a pale greenish-yellow tint of creamy white in the outer terminal end portion of their planar area, and a pale green tint to the peripheral edge portion of the bracts, as said coloration is more particularly described in the color tabulation below. The venation of the bracts is of the herringbone type. The petioles of the bracts are of a pale green hue as compared with the darker green color of the foliage leaves.

The season for optimum development of the bracts is from approximately December 1st to mid-December and they maintain their optimum appearance for an unusually long period, lasting substantially two months, making this new variety a premium display plant for the Christmas market, especially if interspersed with the usual red variety of poinsettia for vivid contrast of color.

*Inflorescence*

A node is formed at the upper axial end of each main stalk or peduncle from which the bract-bearing branches or spurs grow upwardly and expansively apart, being usually three in number, and upon these branches or spurs grow a plurality of flower cyathia on short sub-acaulescent stems. Each cyathium is cup-like and contains a single pistillate flower surrounded by numerous staminate flowers, the pistillate flower pushing upward to the top where the stigma is spread for polination. The cyathia are a pale green color at their base, blending into a pale yellow at the opening of the cup. Alongside of the cyathia are the nectary or nectar cups the open labiate mouth of which is of a more vivid orange tint of yellow than the opening of the cyathia.

*General character of growth*

This new variety of poinsettia plant is further characterized by its strong and luxuriant growth, rendering cultivation and propagation relatively easy under favorable conditions which are standard and normally exercised by those skilled in cultivation of poinsettia plants.

*Variations*

Different plants of this new variety have an unusual similarity of adherence to characteristics and type as herein described. However, there may be some variations in the characteristics of minor detail, in comparison of plants grown in various localities, in different soils and at various times of the year, varying temperatures, varying types of glass houses, or out of doors.

*Color tabulations*

The color designations according to the color plates of said "Dictionary of Color" are recapitulated in tabular form as follows:

| Part of Plant | Non-Technical Designation of Color | Plate | Letter | Number |
|---|---|---|---|---|
| Foliage leaves | Ivy green | 23 | A | 12 |
| Bract-bearing spurs | Pale green | 21 | K | 11 |
| Bracts: | | | | |
| Predominating color | Pale greenish tint of creamy white. | 17 | B | 2 |
| Tinting of planar area of some bracts adjacent outer acuminate terminal end. | Pale greenish yellow tint of creamy white. | 17 | D | 3 |
| Tinting at peripheral edge portion of some bracts. | Pale green | 18 | J | 6 |
| Petioles of bracts | do | 18 | L | 8 |
| Inflorescence: | | | | |
| Cyathia— | | | | |
| at base | light tint of pale green. | 19 | K | 6 |
| at cup opening | pale yellow | 19 | L | 1 |
| Nectar cup labials | Orange tint of yellow. | 10 | K | 5 |

Having described and illustrated my new variety of poinsettia plant, I claim:

A new and distinct variety of poinsettia plant, substantially as illustrated and described, characterized by a central inflorescence and an involucre of a large number of prolately-ovate-acuminate bracts of predominantly a pale greenish tint of creamy white color and of substantially greater width than known varieties, the bracts radiating on relatively short petioles from the inflorescence and the side edges of individual bracts overlapping the side edges of the next adjacent bracts in wreath-like relation.

No references cited.